United States Patent [19]

Slater

[11] Patent Number: 5,241,968
[45] Date of Patent: Sep. 7, 1993

[54] SINGLE ACTING ENDOSCOPIC INSTRUMENTS

[75] Inventor: Charles R. Slater, Fort Lauderdale, Fla.

[73] Assignee: Symbiosis Corporation, Miami, Fla.

[21] Appl. No.: 944,202

[22] Filed: Sep. 11, 1992

Related U.S. Application Data

[63] Continuation-in-part of Ser. No. 680,392, Apr. 4, 1991, Pat. No. 5,192,298, and a continuation-in-part of Ser. No. 780,013, Oct. 21, 1991, and a continuation-in-part of Ser. No. 837,046, Feb. 18, 1992, which is a continuation of Ser. No. 521,766, May 10, 1990, Pat. No. 5,133,727.

[51] Int. Cl.$^5$ .............................................. A61B 10/00
[52] U.S. Cl. .................................. 128/751; 606/205; 606/207; 606/208
[58] Field of Search ............... 128/749, 751, 754, 757; 606/151, 155, 167, 170, 174, 205, 206, 207, 208

[56] References Cited

U.S. PATENT DOCUMENTS

| | | | |
|---|---|---|---|
| 3,828,791 | 8/1974 | Santos | 606/207 |
| 4,122,856 | 10/1978 | Mosior et al. | 606/170 |
| 4,785,825 | 11/1988 | Romaniuk et al. | 606/174 X |
| 4,898,157 | 2/1990 | Messroghli et al. | 606/208 X |
| 4,944,093 | 7/1990 | Falk | 606/174 X |
| 4,950,273 | 8/1992 | Briggs | 606/205 X |
| 5,147,373 | 9/1992 | Ferzli | 606/206 X |
| 5,152,780 | 10/1992 | Honkenen et al. | 128/751 |

Primary Examiner—Lee S. Cohen
Assistant Examiner—Samuel G. Gilbert
Attorney, Agent, or Firm—David P. Gordon

[57] ABSTRACT

Surgical instruments of the invention are provided with distal ends having a clevis and two discrete investment cast end effectors. One end effector is stationary relative to the clevis, and the other moves or rotates about a transverse pin of the clevis. The rotating end effector includes a first hole through which the transverse pin extends, and the surgical instrument includes an actuation mechanism for causing the rotating end effector to rotate about the transverse pin. The actuation mechanism preferably includes a push rod which is either directly coupled to the proximal end of the rotating end effector or coupled by a staple element. On the other hand, the stationary second end effector, while including a first hole through which the transverse pin extends, has a boss which preferably engages a hole in the clevis and is not coupled to the actuation mechanism. With the clevis and second end effector being coupled at two locations, the second end effector is not free to rotate about the clevis pin, but is held stationary. Other manners of holding the second end effector stationary are to provide the clevis with a boss, and the stationary end effector with a second hole into which the boss extends, or to provide another pin which extends through one arm of the clevis and the stationary end effector only.

20 Claims, 4 Drawing Sheets

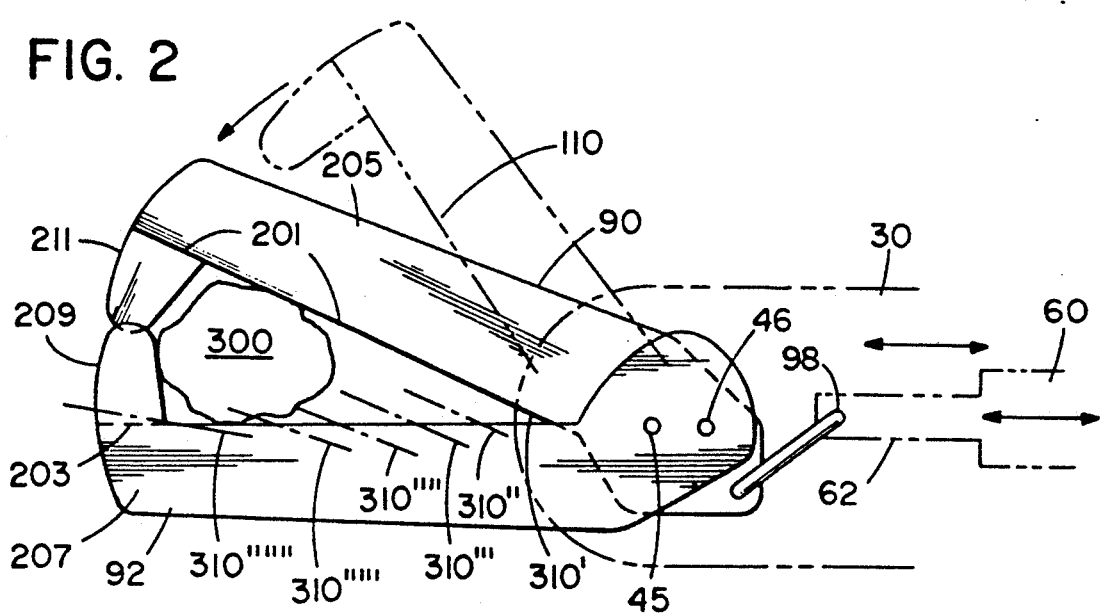
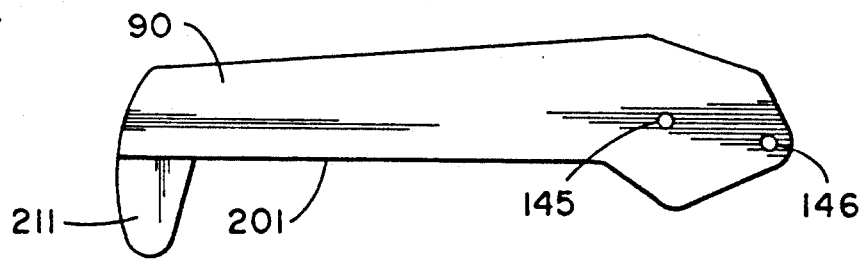
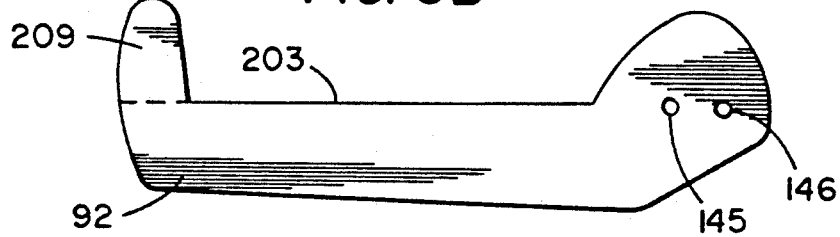
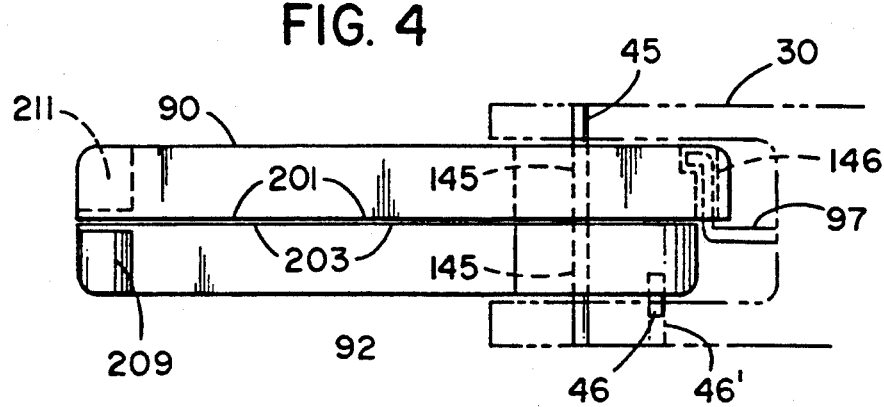

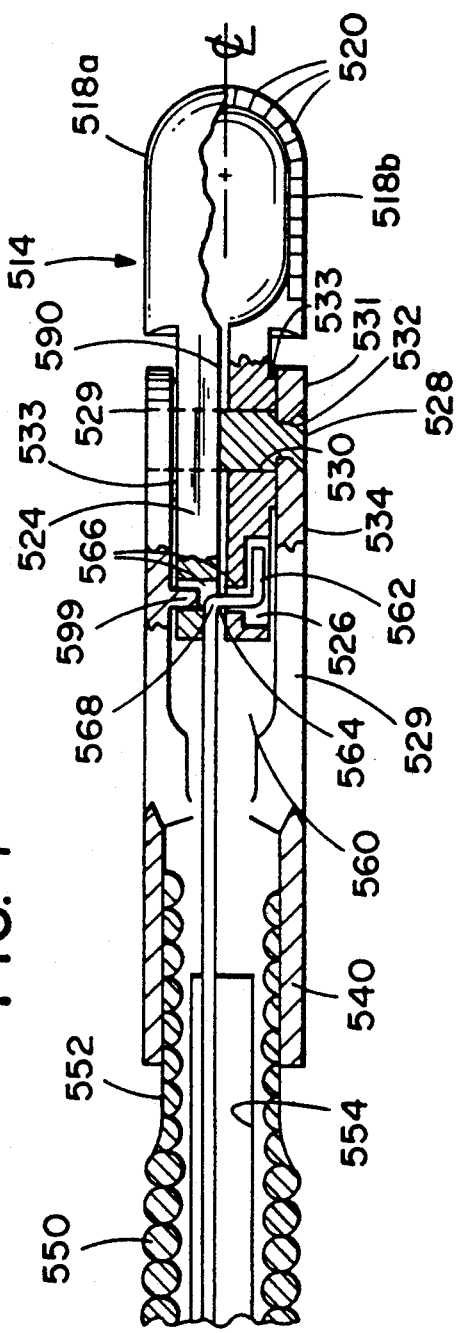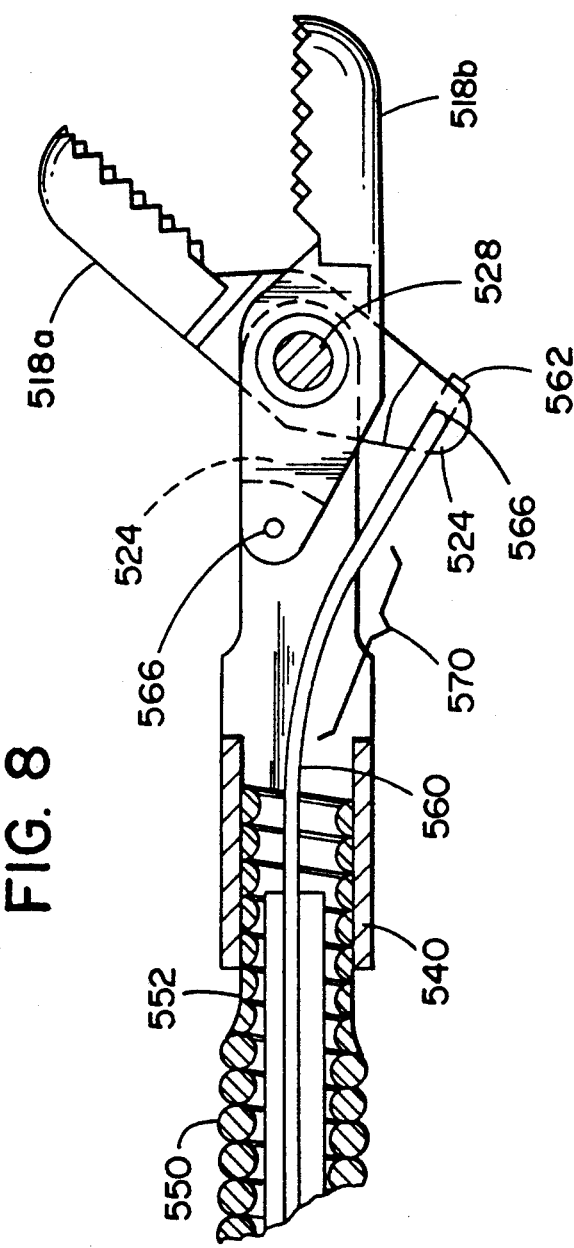

SINGLE ACTING ENDOSCOPIC INSTRUMENTS

This a continuation in part of copending U.S. Ser. Nos. 07/680,392, filed Apr. 4, 1991, now U.S. Pat. No. 5,192,298, and 07/780,013, filed Oct. 21, 1991, and of U.S. Ser. No. 07/837,046, filed Feb. 18, 1992 which is a continuation of Ser. No. 07/521,766, filed May 10, 1990, now issued as U.S. Pat. No. 5,133,727, all of which are assigned to the assignee hereof all of which hereby are incorporated by reference herein in their entireties.

BACKGROUND OF THE INVENTION

This invention relates generally to surgical instruments. More particularly, this invention relates to endoscopic surgical instruments having end effectors with a stationary element and a articulating element.

The endoscopy and laparoscopy procedures have recently become widely practiced surgical procedures. A laparoscopy procedure typically involves incising through the navel and through the abdominal wall for viewing and/or operating on the ovaries, uterus, gall bladder, bowels, appendix, although more recently, incisions and insertion of trocar tubes have been made in different areas of the abdomen and even in the chest cavity. Typically, trocars are utilized for creating the incisions. Trocar tubes are left in place in the abdominal wall so that laparoscopic surgical tools may be inserted through the same. A camera or magnifying lens is often inserted through the largest diameter trocar tube (e.g. 10 mm diameter) which is generally located at the navel incision, while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

Different classes of endoscopic and laparoscopic tools are known in the art, including cutters (scissors), dissectors, graspers, clamps, etc. Among the classes of tools, it is known that tools can be double acting or single acting; i.e., either both of the end effectors at the end of the tool move (double acting), or only one of the end effectors move (single acting). Previous to the present invention, the single acting instruments of the art incorporated the stationary end effector as an integral element of the clevis of the instrument. Examples of such single acting instruments where the stationary end effector is integral with the clevis include a claw forceps, straight scissors, and a hook scissors, all of which are disclosed in Chapter 2 ("Laparoscopic Equipment and Instrumentation" by Talamini and Gadacz) of *Surgical Laparoscopy*, edited by Karl A. Zucker, Quality Medical Publishing, Inc., St. Louis, Mo. (1991). While the prior art design of incorporating the stationary end effector with the clevis has been effective in obtaining the desired result, i.e., that only a single end effector moves, the design is expensive to manufacture (typically being stainless steel). The expensive nature of the instrument, however, does not lend itself to permitting disposal of the instrument after one use, and disposable instruments are becoming standard in the art due to the difficulty in sterilizing endoscopic and laparoscopic instruments and the risk of spreading disease.

SUMMARY OF THE INVENTION

It is therefore an object of the invention to provide cost effective end effectors for single acting endoscopic and laparoscopic instruments.

It is another object of the invention to provide end effectors for single acting endoscopic and laparoscopic instruments where the end effectors are discrete components and are similar to each other.

It is a further object of the invention to provide investment cast discrete end effectors for single acting endoscopic and laparoscopic instruments.

Another object of the invention is to provide discrete end effectors for single acting endoscopic and laparoscopic instruments where the stationary end effector includes a boss for preventing rotational movement of the stationary end effector.

In accord with the objects of the invention, the endoscopic and laparoscopic instruments of the invention are provided with distal ends having a clevis and two discrete end effectors. One end effector is stationary relative to the clevis, and the other end effector moves or rotates about a transverse pin of the clevis. The rotating end effector includes a first hole through which the transverse pin extends, and the instrument of the invention includes actuation means for causing the rotating end effector to rotate about the transverse pin. The actuation means preferably includes a push rod which is either directly coupled to the proximal end of the rotating end effector or coupled by means of a staple or link element. On the other hand, the stationary second end effector, while including a first hole through which the transverse pin extends, has a boss which preferably engages a hole in the clevis and is not coupled to the actuation means. With the clevis and second end effector being coupled at two locations, the second end effector is not free to rotate about transverse clevis pin, but is held stationary. Another manner of holding the second end effector stationary is to effectively reverse the boss and hole; i.e., to provide the clevis with a boss, and the stationary end effector with a second hole into which the boss extends; or to provide a screw which is inserted from outside the clevis and into a threaded hole in the stationary end effector.

In accord with a preferred aspect of the invention, the end effectors are investment cast end effectors which are particularly cost effective. The investment cast material may be a bronze alloy, a cobalt base alloy, or another material which can be cast and provide desired strength. The end effectors of the invention may be scissors, graspers, clamps, dissectors, forceps, or any other types of end effectors known in the art, provided that they comprise two discrete components and one of them is rendered stationary. Also, the instrument of the invention may be a laparoscopic type tool with a longitudinal tube through which the push rod extends, or an endoscopic type tool with a flexible coil or the like and through which an actuation wire extends, or any other similar type surgical tool where the end effectors are nonintegral with and remote from the handle or means which causes movement of the rotating end effector.

A better understanding of the single acting instruments of the invention, and additional advantages and objects of the invention will become apparent to those skilled in the art upon reference to the detailed description and accompanying drawings.

BRIEF DESCRIPTION OF THE DRAWINGS

FIG. 2 is an enlarged side elevation view of the end effectors of the invention of the hook scissors embodiment of FIG. 1 in an open position;

FIGS. 3a and 3b are enlarged elevation views respectively of the rotating and stationary blades of the device of FIG. 2;

FIG. 4 is an enlarged elevation view of the device of FIG. 2 in the closed position;

FIG. 7 is a plan view partly in section of the distal end of the single acting forceps of FIG. 5 in a closed position; and FIG. 8 is a side elevation view partly in section of the single acting biopsy forceps of FIG. 3 in an open position.

DETAILED DESCRIPTION OF THE PREFERRED EMBODIMENT

Figure 1:
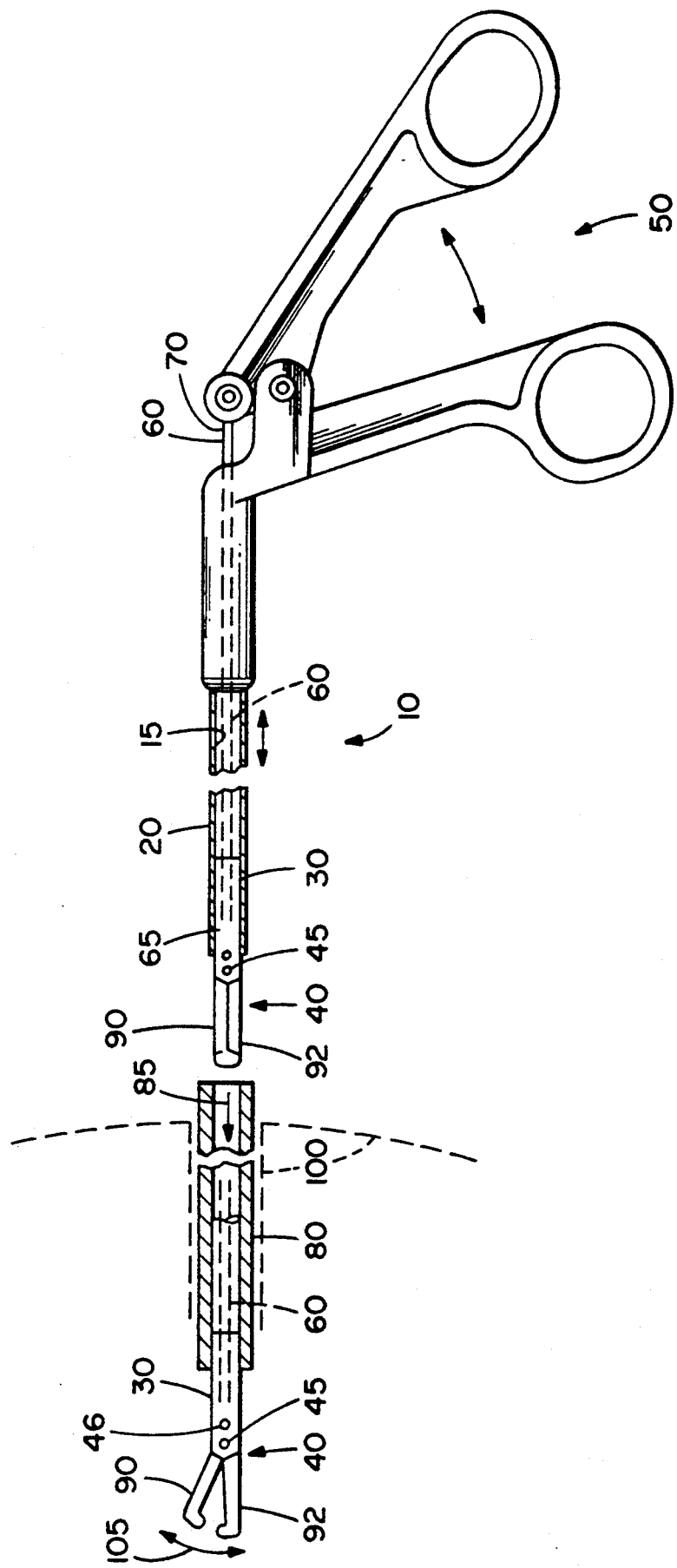
FIG. 1 is a side elevation view, partly in section, of a single acting laparoscopic hook scissors instrument prior to insertion into a trocar tube, and, in partial phantom format, after insertion into a trocar tube.

With reference to FIG. 1, a laparoscopic surgical instrument intended for single use is indicated at 10. The laparoscopic surgical instrument 10 includes a hollow aluminum tube 15 surrounded by a peripheral insulating shrink wrap layer of plastic 20, a clevis means 30, end effector means 40, handle actuators 50, and a push rod 60. The clevis means 30 is preferably a separately formed aluminum piece which fixedly engages aluminum tube 15. The clevis 30 also engages the manipulating members 90, 92 of the end effector means 40. Movable member 90 is pivotally engaged to clevis 30 at pivot pin 45 and stationary member 92 is fixedly engaged to the clevis 30 at pin 45 and post 46 as described in more detail hereinafter. End effectors 90, 92 are preferably formed via investment casting techniques and the preferred material for the scissors of FIG. 1 is a cobalt base alloy, although it can be formed of other materials such as, e.g., a bronze alloy or stainless steel, if desired. The push rod 60, which is preferably formed of aluminum or stainless steel, is engaged at its distal end 65 to the end effector means 40, as hereinafter more fully described, and is connected at 70, at its proximal end, to a manually operable actuating mechanism 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the blades 90, 92 of the end effector means 40, in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, bade 90 can be opened and closed as indicated at 105 by reciprocal motion of push rod 60 which results from operation of the manual actuating means 50. As is discussed in more detail in parent application Ser. No. 07/680,392, the clevis effectively helps to translate the reciprocal motion of the push rod 60 into the end effector means action indicated at 105.

Additional detail regarding the laparoscopy instrument 10 may be obtained by reference to previously incorporated parent application Ser. Nos. 07/680,392, and 07/780,013.

With reference to FIG. 2, the hook scissors end effector of the present invention is shown at 110 in an open position having a pivotally rotatable blade member 90 which is rotatable about pivot pin 45 of clevis 30 as more fully described hereinafter. Blade member 92 preferably also engages the pivot pin 45. However, because blade member 92 is provided with a post 46 which engages a hole 46' (see FIGS. 4 and 5) in clevis 30, blade member 92 is fixed in position with respect to clevis 30. Blade members 90, 92 are held in a tight bearing contact by pivot pin 45 which extends through holes 145 of the blade members and which engages the clevis 30. Each blade member 90, 92 has a respective straight cutting edge 201, 203 which extends along blades 90, 92 to their distal portions 205, 207 remote from the pivotal engagement at 45.

As seen in FIGS. 3a and 3b, the hook scissors end effectors are comprised of similar blade members 90, 92 (minor differences including the provision of a projection or post 46 on member 92 for insertion into a hole 46' in the clevis, the elimination hole 146 on member 92 for a connecting means being provided where one blade member is fixed, and a slightly differently shaped proximal base portion). As seen in FIGS. 2, 3a, and 3b, each elogate straight blade member 90, 92 has a transverse integral hook element 209, 211. The hook elements 209, 211 extend toward each other in the open position of FIG. 2 and are offset from their respective blade members as seen in FIG. 4) so as to provide a narrow recess between the opposing hook elements when the blade members are closing or in the closed position.

In use, blade 90 can be opened relative to blade 92 as shown in phantom in FIG. 2, such that a tissue, vein, duct, or other object 300 can be gently grabbed by the hook element 209 of blade 92 and/or by the hook element 211 of blade 90. By closing blade 90 relative to blade 92 as shown in FIG. 2, object 300 is encompassed by the non-sharpened, non-contacting, blunt edged, parallel, opposed hook elements 209, 211. With the object 300 so encompassed (or with hook element 209 grabbing the object as in the case of a vein or other small object), the object can pulled to a location where positive identification by imaging or other equipment is achieved. When the identity of the encompassed object is identified, and cutting is desired, the cutting operation along cutting edges 201, 203 proceeds by pivotal movement of blade member 90. With the device of the present invention, a clean cut is provided by cutting edges 201, 203 as blade member 90 and 92 contact each other along a continuously moving bearing contact point 310'- 310"- 310'''-310''''-310'''''- 310''''', thereby avoiding entrapment of tissue between laterally displaced blade members. Also, since cutting proceeds from one end only, the accidental cutting of an object which can happen in the prior art hook scissors is avoided during the procedure of grabbing the object, as the opposed hook elements 209, 211 do not act to cut.

Figure 5:
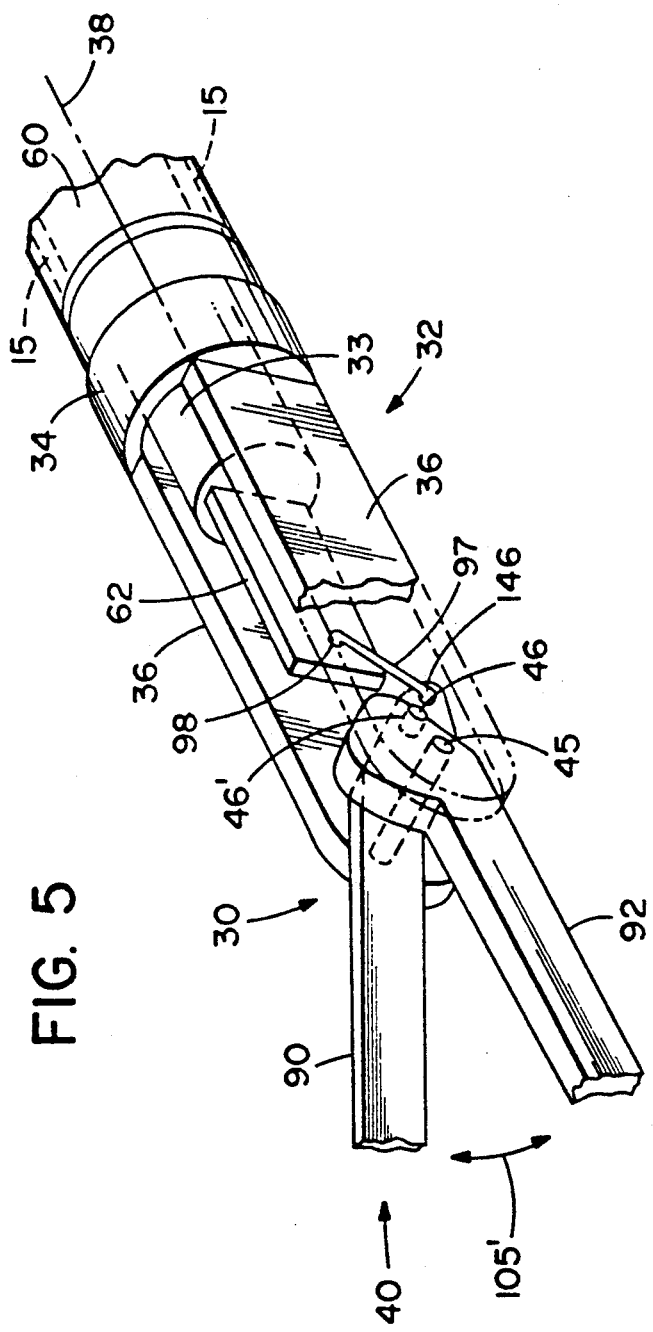
FIG. 5 is a perspective view of a clevis element usable with the single acting hook scissors of FIG. 1.

Turning to the perspective view of FIG. 5, a preferred configuration of the clevis 30 for use with the present invention is seen. The clevis has a knurled rod-like proximal portion 34 for mating with the end of the aluminum tube 15, and a pivotsupporting U-shaped distal portion 32 for holding the end effector means 40 comprising members 90, 92. The proximal portion 34 of the clevis is preferably hollow, as indicated at 33, to permit the push rod 60, with its flattened terminal portion 62 to extend therethrough. The distal portion 32 of the clevis 30 is provided with a pivot pin 45 which is generally perpendicular, i.e. transverse, to the legs 36 of the clevis. In addition, in accord with the preferred embodiment of the invention, at least one of legs of clevis 30 is provided with a hole 46'. The fixed end effector blade 92 of the single acting instrument is provided with the a transverse or lateral protrusion or boss 46 which extends into hole 46'. As a result, fixed blade 92 is fixed relative to the clevis 30 by engagement of protrusion 46 in hole 46' and by engagement of hole 145 at pivot pin 45. On the other hand, the pivoting blade member 90 is engaged at through hole 146 by a metal link member 97 to push rod 60 which is engaged to link member 97 at through hole 98. Upon actuation of push rod 60, blade member 90 moves pivotally around pin 45 to provide the scissor action indicated at 105' while blade member 92 remains stationary.

As aforementioned, the end effectors of the invention are preferably formed of investment cast metal such as cobalt base alloy or bronze. The advantage of casting the end effectors utilizing the investment cast technique or any other casting technique is that all the features of the end effectors are formed during casting in an integral end effector element. This is in contrast with the prior art practice of stainless steel end effectors which involved forging and machining to achieve the desired finished forms. Thus, the investment casting of the end effectors eliminates the need for forging and machining and also abrasive blasting and pickling and other treatments required in stainless steel fabrication which is costly and which interferes with the achievement of close tolerances. It is noted that where bronze is used for the end effectors, since bronze is not as strong as stainless steel, it is advantageous to provide integral reinforcing elements in the investment cast end effector as described in greater detail in parent application Ser. No. 07/680,392. Of course, where a cobalt base alloy is used, as described in detail in commonly assigned Ser. No. 07/780,034 which is hereby incorporated by reference herein in its entirety, the reinforcing elements are not necessarily helpful.

Figure 6:
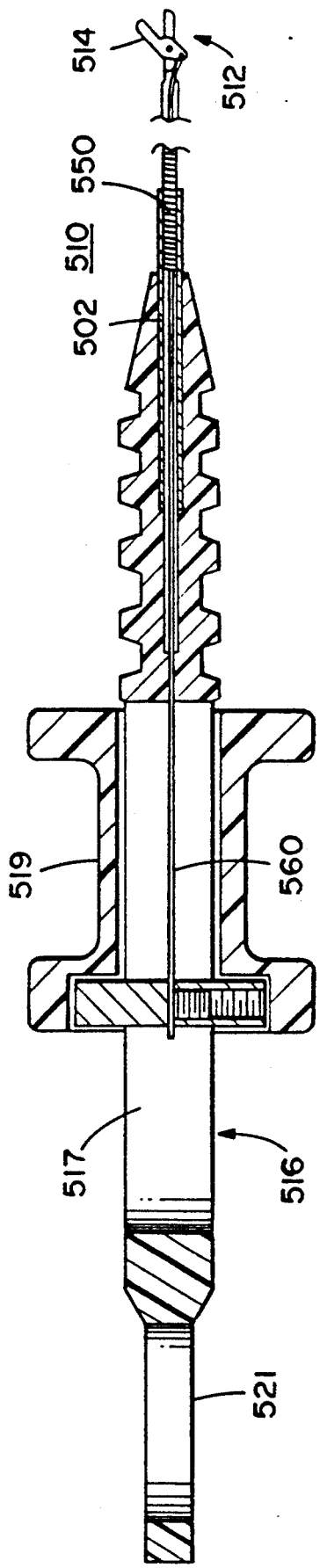
FIG. 6 is a side elevational view in section, of a single acting endoscopic biopsy forceps instrument.

Turning to FIGS. 6, 7 and 8, a single acting biopsy forceps assembly 510 is shown, having a distal end 512 with a jaw assembly 514, a proximal end 516 with a handle 517, a spool 519 and a thumb ring 521 for manipulation of the assembly, and a coil 550 with wire 560 extending therethrough. The jaw assembly 514 comprises a pair of jaws 518a, 518b, each of which is preferably a duplicate of the other, and each of which are preferably formed using investment casting techniques. As may be seen in FIGS. 7 and 8, the jaws are generally elongated somewhat hemispherically shaped structures having distal ends and proximal ends. On the distal end, each jaw 518a, 518b an array of teeth 520 generally radially directed about a point "R", as exemplified in FIG. 7. Also, each jaw 518 has a generally longitudinal centerline as may be seen in FIGS. 7. As disclosed in detail in parent application Ser. No. 07/837,046, the teeth 520 on one side of the longitudinal centerline of each jaw 518a, 518b are displaced by one half pitch from the corresponding teeth 520 on the other side of the longitudinal centerline on that jaw. The displacement by one half pitch by the teeth on one side of the jaw is relative to those corresponding teeth 520 on the other longitudinal side of the jaw permits the same casting to be used for both the upper and lower jaws of the jaw assembly 514. The radial arrangement of the teeth 520 permits the jaws 518a, 518b to automatically mate and effectuate proper alignment therebetween when the rotating jaw closes onto the stationary jaw.

As disclosed in the parent application Ser. No. 07/837,046 each jaw 518a, 518b is preferably manufactured by an investment casting technique which is inherently less expensive than the typical prior art jaws which are machined. In addition, with investment casting, each jaw can have teeth 520 extending around the distal periphery of the jaw, thereby providing a positive cutting edge. This arrangement is in contrast to the prior art devices which either do not have teeth at the very distal end of the jaw or which have distal teeth which are transverse to the longitudinal centerline the jaws. The casting of each jaw 518a, 518b also permits a looser tolerance therebetween without any loss in effectiveness.

Returning to FIGS. 7 and 8, it is seen that the jaws 518a, 518b have a tang 524 at their proximal ends. Each tang 524 has a generally semicircular recess position 526 on its outer side thereof, and a hole 566 therein. As hereinafter described, the hole 566 of the tang 524 of the rotating jaw 518a receives the end 562 of pull wire 560, while the hole 566 of the tang 524 of the stationary jaw 518b receives a pin which is coupled to the clevis 534. Each jaw 518a, 518b also includes a bore 530 which extends transversely through the middle section between the distal and proximal ends of the jaw. Extending through the bore 530 is a clevis pin 528 around which the rotating jaw rotates.

The clevis pin 528 is part of the clevis 534 of the biopsy jaw forceps device. The clevis 534 also has a proximal end with a hub or housing 540, side arms 529 which are integral therewith, and preferably an additional boss 599 (it being recognized that boss 599 could actually be a separate pin which extends through a side arm 529). As described hereinafter, the hub 540 receives and mates with the distal end of a long coil 550 while permitting wire 560 to extend therethrough and engage hole 566 of the tang of the rotating jaw. The side arms 529 extend around the proximal ends of the jaws 518 and provide structure for carrying the clevis pin 528 around which the rotating jaw 518a rotates. Preferably, the clevis pin 528 extends in a perpendicular manner through one arm 529 of the clevis, then through bores 530 of the jaws, and then into the other arm of the clevis. The additional boss or pin 599 is provided to extend from the clevis into the hole 566 of the tang of the stationary jaw 518b. In this manner the stationary jaw and the clevis are coupled at a first location by clevis pin 528, and at a second location by boss 599. The provision of the boss therefore prevents rotation of the stationary jaw around clevis pin 528. Additional details regarding other aspects of the clevis may be obtained with reference to previously incorporated parent application Ser No. 07/837,046 which differs from the present invention only in that they does not include boss or pin 599, but includes a second pull wire for causing the second jaw to rotate.

As seen in FIGS. 7 and 8, the distal end of the main tubular coil 550 shown in has a portion of it periphery ground flat, as at 552. The flattened distal periphery of the main coil 550 permits a more solid anchoring between the inside of the hub 540 of the clevis 534 and the distal end of the main coil 550 when the two are crimped together, obviating the need for adhesives, soldering or welding. Also seen is an FEP sheath 554 which extends from the distal end of the main coil 550 therethrough into the central shaft of the handle 517. This sheath 554 acts as a bearing between the pull wire 560 and the lumen of the main coil 550.

With reference to FIG. 7, the distal end of pull wire 560 has a Z-bend therein with a first portion 562 which is rotatably disposed in the recess 526 in the tang 524 of the cutter jaw 518, and a second portion 564 which extends through a bore 566 in the proximal end of the tang 524 of the rotating jaw. A ninety degree bend 568 between the second portion 564 and the main pull wire 560 eliminates the pinching common to prior art loop design wires. Also, the pull wire 560 has a reflex curve 570 as shown in FIG. 8 extending between the main coil 550 and the rotating jaw 518a. The reflex curve 570 helps to open the rotating cutter jaw relative to the stationary cutter jaw when the spool 519 on the handle 517 is displaced distally thereto.

The proximal end of the main coil 550 and the proximal end of the pull wire 560 extend into handle 517 at the proximal end 516 of the biopsy forceps assembly 510. The handle 517 comprises a central shaft about which a displaceable spool 519 is disposed. Details of the proximal end of the biopsy forceps assembly 510 may be seen with reference to previously incorporated parent application Ser. No. 07/837,046, and are not included herein. It is of note that the only difference between the proximal end of the assembly 510 of the parent application and the proximal end of the assembly of the instant invention is that that an extra pull wire is provided in the parent application.

There has been described and illustrated herein single acting endoscopic instruments. While particular embodiments of the invention such as a laparoscopic hook scissors and a biopsy jaw forceps have been described, it is not intended that the invention be limited exactly thereto, as it is intended that the invention be as broad in scope as the art will allow. Thus, it will be appreciated that the the concepts disclosed apply to all different types of endoscopic and laparoscopic tools, including, but not limited to scissors, clamps, forceps, biopsy devices, dissectors, etc. Also, it should be appreciated that the concepts disclosed with reference to the laparoscopic hook scissors can be applied to tools such as the biopsy jaw forceps and vice versa; i.e., different aspects of the embodiments can be mixed and matched. By way of example, instead of providing a boss on the clevis for engaging the stationary jaw of the biopsy jaw forceps, the boss could be formed on the stationary jaw and extend into a hole in the clevis of the forceps. Or, instead of utilizing a staple-like element for coupling the push rod to the rotating scissor element in the laparoscopic scissors, the push rod could be provided with a Z-bend at its distal end and couple directly to the rotating scissor element. Further, while both the laparoscopic hook scissors and the biopsy jaw forceps were shown as having the transverse clevis pivot pin located at the same height as the longitudinal axis of the tool, it will be appreciated that different arrangements such as described in commonly assigned copending application Ser. No. 07/780,014, which is hereby incorporated by reference herein in its entirety, where the clevis pivot pin is offset relative to the longitudinal axis of the tool could be utilized to provide single acting tools with additional leverage. Also, while the stationary end effector of both the laparoscopic hook scissors and biopsy jaw forceps was described as being held stationary via the use of a boss either on the clevis or on the end effector, and a hole in the other of the two into which the boss extends, it will be appreciated that the hole need not be a through-hole, but could rather be an indentation or the like which would stabilize the boss. Alternatively, a separate pin which extends into the clevis and the stationary end effector could be utilized in lieu of the boss. Therefore, it will be apparent to those skilled in the art that other changes and modifications may be made to the invention as described in the specification without departing from the spirit and scope of the invention as so claimed.

We claim:

1. In a surgical instrument having an actuation mechanism including a wire or a push rod element having proximal and distal ends, a clevis having arms and a clevis pin transverse said arms, first and second end effectors with said first end effector coupled to said distal end of said wire or push rod element, and said first and second end effectors having first through-holes through which said clevis pin extends, whereby axial movement of said wire or push rod element is translated to rotational movement of said first end effector, an improvement comprising:
    said first and second end effectors are separate discrete components, and
    said surgical instrument further comprises a coupling means for coupling said clevis and said second end effector at a first location, wherein said second end effector is coupled to said clevis at a second location by said clevis pin, such that said second separate end effector is held stationary relative to said clevis.

2. In the surgical instrument of claim 1, wherein:
    said coupling means comprises
    a boss integral with said second end effector and extending substantially parallel said clevis pin, and
    a hole in said clevis into which said boss extends.

3. In the surgical instrument of claim 2, wherein:
    said separate discrete first and second end effectors are castings.

4. In the surgical instrument of claim 1, wherein:
    said coupling means comprises
    a boss integral with said clevis and extending substantially parallel said clevis pin, and
    a second hole in said second end effector into which said boss extends.

5. In the surgical instrument of claim 4, wherein:
    said separate discrete first and second end effectors are castings.

6. In the surgical instrument of claim 1, wherein:
    said coupling means comprises
    a second pin,
    a first hole in said clevis, and
    a second hole in said second end effector, with said second pin extending into said first hole in said clevis and into said second hole in said second end effector.

7. In the surgical instrument of claim 6, wherein:
    said second pin comprises a screw, and
    said second hole in said second end effector is a threaded hole which receives said screw.

8. In the surgical instrument of claim 6, wherein:
    said separate discrete first and second end effectors are castings.

9. In the surgical instrument of claim 1, wherein:

said separate discrete first and second end effectors are castings.

10. In the surgical instrument of claim 9, wherein:
said surgical instrument further comprises a hollow tube having distal and proximal ends and a longitudinal axis,
said wire or push rod element comprises a push rod extending at least partially through said hollow tube and coupled to said first end effector, and
said clevis is coupled to said hollow tube.

11. In the surgical instrument of claim 10, wherein:
said surgical instrument further comprises linkage means for coupling said push rod to said first end effector, said linkage means having first and second end portions and a middle portion, said push rod having a hole at its distal end through which said first end portion of said linkage means is coupled, and said first end effector, having a second hole in its proximal end through which said second end portion of said linkage is coupled.

12. In the surgical instrument of claim 9, wherein:
said surgical instrument further comprises a flexible main coil, and said wire or push rod element comprises a wire which extends through said flexible main coil and is coupled to said first end effector.

13. In the surgical instrument of claim 12, wherein:
said flexible main coil has distal and proximal ends, and said surgical instrument further comprises a handle disposed on said proximal end of said main coil.

14. A surgical instrument suitable for insertion through a trocar tube, comprising:
a) a hollow tube having proximal and distal ends and a longitudinal axis;
b) a clevis mechanically coupled to said distal end of said hollow tube, said clevis including a pin extending transverse said longitudinal axis;
c) first and second discrete end effectors, each said end effector having a first through-hole in its proximal portion for engaging said pin at first locations, and said clevis and second end effector having coupling means for engaging said clevis with said second end effector at a second location, thereby rendering said second end effector stationary relative to said clevis;
d) a rod extending at least partially through said hollow tube and having a distal end and a proximal end, said rod being coupled to said first end effector; and
e) actuating means engaging said proximal end of said rod for imparting reciprocal motion to said rod relative to said hollow tube which is translated to pivotal motion of said first end effector around said pin.

15. A surgical instrument according to claim 14, wherein:
said coupling means for engaging said clevis with said second end effector comprises
a boss integral with said second end effector and extending substantially parallel said clevis pin, and
a hole in said clevis into which said boss extends.

16. A surgical instrument according to claim 14, wherein:
said coupling means for engaging said clevis with said second end effector comprises
a boss integral with said clevis and extending substantially parallel said clevis pin, and
a second hole in said second end effector into which said boss extends.

17. A surgical instrument according to claim 14, wherein:
said coupling means for engaging said clevis with said second end effector comprises
a second pin,
a first hole in said clevis, and
a second hole in said second end effector, with said second pin extending into said first hole in said clevis and into said second hole in said second end effector.

18. A surgical instrument according to claim 17, wherein:
said second pin is a screw, and
said second hole in said second end effector is a threaded hole which receives said screw.

19. A surgical instrument according to claim 14, wherein:
said first and second discrete end effectors are castings.

20. A surgical instrument according to claim 14, further comprising:
a linkage means for coupling said distal end of said rod with said first end effector, said linkage means having first and second end portions and a middle portion, said rod having a through-hole in said distal end of said rod with said first end portion of said linkage means coupled thereto, and said first end effector having a second through-hole with said second end portion of said linkage means coupled thereto.

* * * * *